United States Patent [19]

Shum

[11] Patent Number: 4,962,266

[45] Date of Patent: Oct. 9, 1990

[54] PROCESS TO CONVERT LINEAR ALKANES

[75] Inventor: Victor K. Shum, Naperville, Ill.

[73] Assignee: Amoco Corporation, Chicago, Ill.

[21] Appl. No.: 401,978

[22] Filed: Aug. 31, 1989

[51] Int. Cl.$^5$ .......................... C07C 5/333; C07C 5/13
[52] U.S. Cl. .................................. 585/660; 585/661; 585/670; 585/751
[58] Field of Search ................ 585/660, 661, 670, 751

[56] References Cited

U.S. PATENT DOCUMENTS 4,329,328  5/1982  McAnespie et al. ................ 502/243
4,538,017  8/1985  Butler et al. ........................ 585/660

Primary Examiner—Curtis R. Davis
Attorney, Agent, or Firm—Ekkehard Schoettle; William H. Magidson; Ralph C. Medhurst

[57] ABSTRACT

The invention relates to a process for the conversion of linear alkanes such as n-butane to dehydrogenated and isomerized products in the presence of a catalyst comprising a platinum component and a zincosilicate component.

19 Claims, 1 Drawing Sheet

CONVERSION VERSUS TIME FOR Pt/Zn-SILICATE AND Pt/Al$_2$O$_3$

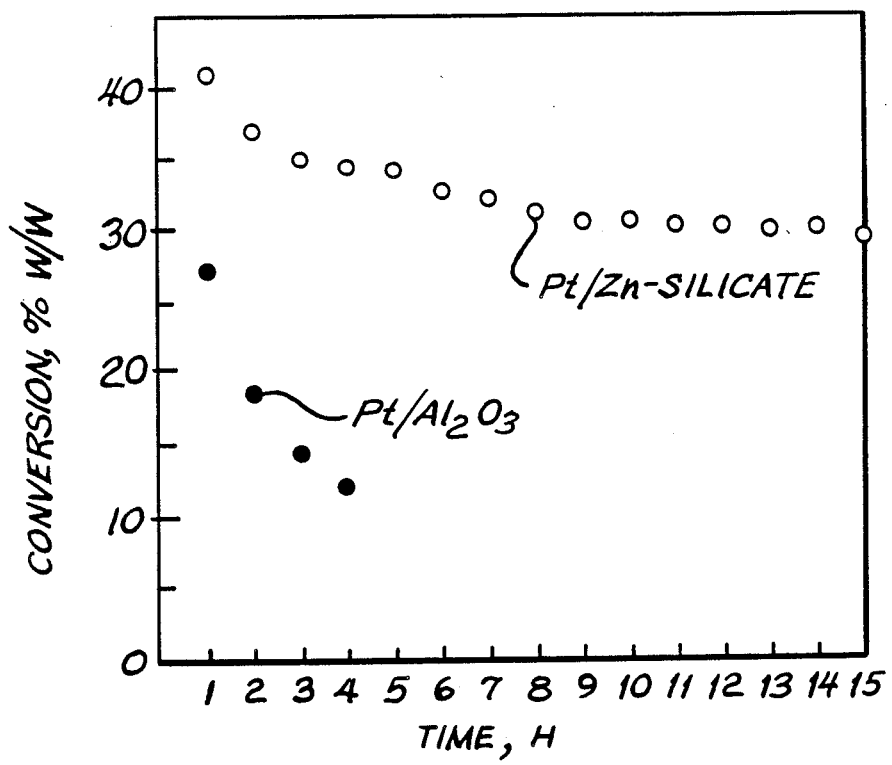
CONVERSION VERSUS TIME FOR Pt/Zn-SILICATE AND Pt/Al₂O₃

PROCESS TO CONVERT LINEAR ALKANES

BACKGROUND OF THE INVENTION

This invention relates to conversion of linear alkanes, such as n-butane, and more particularly relates to conversion of n-butane to higher value hydrocarbons such as butylenes, isobutane and aromatics using a catalyst composition comprising a platinum metal component and a zincosilicate component.

In many instances it is desirable to convert an alkane such as linear alkane or a molecule containing a linear alkane segment into an alkene by dehydrogenation, a branched molecule by structural isomerization, or an aromatic species. Such alkenes and branched molecules then can be reacted further such as by polymerization or oxidation to form useful products. Normal butane is a linear alkane containing four carbon atoms which is obtained commercially by separation from natural gas and as a petroleum refinery by-product. Further, as government regulations mandate a reduction in the reid vapor pressure (RVP) of gasoline, an excess of light gases such as butane arises.

Other reasons for an increased supply of light paraffins such as n-butane include the higher severity operation of the reforming process in order to maintain a high octane rating in the absence of or reduction of the lead content in gasoline, the increased use of oxygenates such as methyl tertiary butyl ether (MTBE) and ethanol resulting in the removal of butanes from the gasoline pool, the increased demand for jet fuel necessitating increased gas oil hydrocracking resulting in more light gas production, and the increase in operating temperatures in fluidized catalytic crackers also resulting in more light gas production. Thus, there is a great incentive to investigate means for converting these materials into more valuable liquids such as transportation fuels or chemical feedstocks. As such, n-butane is a relatively inexpensive feedstock.

N-butylenes and isobutylene are both useful in isobutane alkylation to produce high-octane isoparaffinic gasoline. Isobutylene is a branched four-carbon olefin monomer useful in the manufacture of polyisobutylenes which can have various properties depending on the manner of polymerization. For example, both crystalline polyisobutylene and viscous polyisobutylene can be manufactured according to well-known processes in the art. In addition, isobutylene is used in the manufacture of methyl-t-butyl ether which is useful as an octane booster in gasoline. Conventionally, butylenes, including isobutylene, are obtained as a by-product from refinery processes such as catalytic or thermal cracking units.

The prior art teaches various dehydrogenation processes employing catalysts containing a platinum component and/or a zinc-containing component wherein the zinc component is either in an amorphous phase or associated with a crystalline molecular sieve.

U.S. Pat. No. 4,260,839 (Chen et al.) discloses a process for converting ethane to $C_3+$ hydrocarbons using a catalyst comprising a ZSM-5 type aluminosilicate containing a minor amount of added zinc in combination with a Group VIII noble metal or Group IB metal wherein the metals have been incorporated into the catalyst in any convenient process such as impregnation, deposition, or ion-exchange.

U.S. Pat. No. 3,875,253 (Huang) discloses a process for dehydrogenating normal paraffins using a catalyst comprising cobalt, zinc or mixtures or oxides thereof and one or more noble metals of the platinum or palladium families deposited on a low acidity alumina.

U.S. Pat. No. 3,941,871 (Dwyer et al.) discloses crystalline metal organosilicates that are free of aluminum and/or gallium and possess an X-ray diffraction pattern similar to that of ZSM-5 zeolites. Example 10 of the subject patent describes a crystalline organosilicate containing both zinc and sodium. The patent further discloses that the family of crystalline metal organosilicates can contain a hydrogenation component such as platinum and be used for hydroisomerization of normal paraffins and olefin isomerization.

U.S. Pat. No. 3,539,651 (Hepp et al.) discloses a catalytic dehydrogenation process employing a catalyst that contains platinum and zinc aluminate.

U.S. Pat. No. 3,600,332 (Hunter et al.) discloses an alkane dehydrogenation catalyst containing platinum group metal ions exchanged onto an aluminosilicate zeolite, a pore size less than about 5 Å.

U.S. Pat. No. 3,755,198 (Stratenus) discloses a catalyst-containing zinc added to a supported noble metal suitable for use in the dehydrogenation of paraffins to monoolefins.

Another dehydrogenation catalyst is disclosed in U.S. Pat. No. 3,790,504 (Duhaut et al.) which catalyst contains platinum, iridium, and zinc or a zinc compound supported on a carrier such as alumina. U.S. Pat. No. 3,880,776 (Box, Jr. et al.) discloses a dehydrogenation catalyst containing a Group VIII metal supported on a zinc aluminate spinel.

European Patent Application No. 0 124 998 discloses a crystalline zincosilicate having a structure strongly resembling a Theta-1 aluminosilicate. The zincosilicate may also be loaded with metals via ion-exchange, mixing and/or impregnation, these metals being selected from the group consisting of Groups IB, IIIB, IIIA, IVA, VA, VB, VIIB and VIII. The specific metals listed include copper, silver, zinc, alumina, gallium, indium, thallium, lead, antimony, bismuth, chromium, molybdenum, tungsten, manganese, iron, cobalt, nickel, ruthenium, rhodium, palladium, iridium, platinum, rhenium, and the rare earths. The zincosilicate-containing catalysts can be used for any of the following reactions: alkylation, dealkylation, transalkylation of aromatics, dehydrocyclodimerization, aromatization, isomerization, dehydrogenation, hydrogenation, cracking, hydrocracking, cyclization, oligomerization, polymerization, etherification, and dehydration.

In a paper entitled "Effective Conversion of Paraffins to Aromatics on Pt Ion-Exchanged Ga- and Zn-Silicates," T. Inui et al., *Studies of Surf. Sci. Catal.*, No. 37, Innovation in Zeolite Materials Science 1988, pp. 487 through 494, a platinum-Zn-silicate catalyst is disclosed that effects the conversion of paraffins to aromatics. The paper states that all of the X-ray diffraction patterns of Zn-silicates with different Si/Zn ratios were similar to that of H-ZSM-5, indicating that the Zn-silicate has a pentasil structure. The subject sieves were prepared by using the rapid crystallization method wherein the authors maintain that zinc is incorporated in the crystal structure. The authors further maintain that the selective conversion of light paraffins to aromatics is effected first by the dehydrogenation of paraffin to olefin accelerated by platinum. These olefins are then selectively converted to aromatics with the assistance of zinc. The selectivity to aromatics is reported to be about 47 wt.%.

Another paper entitled "Zinc and Aluminum Substitutions in MFI-Structures; Synthesis, Characterization and Catalysis," W. J. Ball et al. *Studies Surf. Sci. Catal.*, No. 28, New Dev. Zeolite Science Technology (1986), pp. 951–956, discloses a catalyst that contains zinc substituted into the MFI framework of a molecular sieve. The subject MFI zincosilicates were used to crack n-hexane. The paper observed that nonframework zinc species dehydrogenate n-hexane thereby reducing the activation energy for cracking over zincosilicates.

The traditional alkane dehydrogenation processes have several drawbacks. The UOP Oleflex ™ process as disclosed in, "Oleflex: $C_2$–$C_5$ Dehydrogenation Updated," B. V. Vora et al., *Energy Progress*, Vol. 6, No. 3, 1986, pp. 171 through 176, employs a platinum-containing catalyst and requires a hydrogen recycle stream to maintain catalyst stability. The chromia/alumina catalyst employed in the Catofin ™ process as disclosed in, "Catalytic Dehydrogenation of Liquefied Petroleum Gas by the Houdry Catofin ™ and Catadiene ™ Processes," R. G. Craig et al., R. A. Meyers (Ed.), Handbook of Petroleum Refining Process, McGraw-Hill, 1986, pp. 4-3 through 4-21 requires frequent regeneration.

Dehydrogenation reactions are fast and reversible. They are limited by thermodynamic equilibria constraints. Low pressures and high temperatures shift the equilibria favorably toward dehydrogenated products. However, conventional platinum- and chromia-containing catalysts suffer rapid deactivation by coking under these severe conditions.

Thus, there is a need for an improved light paraffin dehydrogenation process wherein the catalyst system maintains stability, preferably without hydrogen circulation.

There are several advantages afforded by the decreased use or the lack of use of a hydrogen diluent. Specifically, the dehydrogenation process becomes more economically attractive as the amount of hydrogen used is decreased. Further, as mentioned above, if the partial pressure of hydrogen is reduced or eliminated, the yield of dehydrogenated products is increased because the thermodynamic equilibrium constraints of the dehydrogenation process favor product formation at lower reaction pressures.

Accordingly, the present invention provides for an improved dehydrogenation process wherein the catalyst possesses a high degree of stability with or without a hydrogen diluent in the feedstream, and possesses a high selectivity towards olefins.

SUMMARY OF THE INVENTION

Briefly stated in a broad aspect, the present invention relates to a process for converting alkanes, such as n-butane, to dehydrogenated and isomerized products in the presence of a catalyst comprising a platinum metal component and a zincosilicate component comprising a high surface area, zinc-modified, crystalline silica molecular sieve, essentially aluminum free, incorporated into an inorganic matrix. The zincosilicate component is made in such a way that the zinc content of the sieve, while small, is incorporated differently in the crystalline lattice than zinc-containing sieves made by ion exchange or impregnation processes.

BRIEF DESCRIPTION OF THE DRAWINGS

FIG. 1 shows a plot of fractional n-butane conversion versus time-on-stream for both the process of the invention and a comparative process.

DETAILED DESCRIPTION OF THE INVENTION

This invention is a method to convert an alkane, especially a linear alkane, to a mixture of alkenes, branched alkanes and alkenes, and aromatics. More particularly, this invention is a method to convert n-butane to a mixture containing isobutylene, isobutane and n-butene using a catalyst system containing a platinum metal component and a zincosilicate component.

Alkanes are saturated hydrocarbons, i.e., molecules containing carbon and hydrogen atoms with the carbon atoms linked through carbon-carbon single bonds.

A normal alkane contains a chain of unbranched carbon atoms and is represented by the formula:

$$H_3C(CH_2)_{n-1}CH_3$$

wherein n is an integer ranging from one about 20. Other hydrocarbon-based molecules can have a segment containing a linear alkane structure such as represented by:

$$H_3C(CH_2)_nR$$

wherein R is an organic moiety and n is an integer ranging from one to about 20.

An isoalkane contains a methyl group branched at the end of a linear alkane segment as represented by $$\begin{array}{c} CH_3 \\ | \\ H_3C-CH-(CH_2)_nR \end{array}$$

wherein R is an organic moiety or hydrogen and n is an integer ranging from zero to about 20.

Alkanes which can be converted using the process of this invention include linear alkanes containing up to about 20 carbon atoms such as ethane, propane, n-butane, n-pentane, n-hexane, n-heptane, n-octane, n-nonane, n-decane and n-dodecane. Other suitable alkanes containing up to about 20 carbon atoms include isoalkanes such as isobutane, 2-methylbutane, 2-methylpentane, 2-methylhexane and the like.

For the purposes of this invention, a substantially linear alkane includes normal alkanes, hydrocarbon-based molecule containing a linear alkane segment and isoalkanes as described above. Also included, for the purposes of this invention, is isobutane. The preferable substantially linear alkane useful in this invention is n-butane. Mixtures of substantially linear alkanes can be used in the process of this invention.

The substantially linear alkanes, or mixtures thereof, used in the process of this invention can be converted in the presence of other substances such as other hydrocarbon-based molecules. Thus, a feedstream used in the process of this invention comprising a substantially linear alkane also can contain other hydrocarbons such as alkenes, methane, aromatics, hydrogen, and inert gases. A process in which partially reacted hydrocarbons are recycled will contain a mixture including alkanes, alkenes, methane and aromatics. Typically, a substantially linear alkane feedstream used in this invention contains about 10 to 100 wt.% substantially linear alkane and preferably contains about 50 to 100 wt.% substantially linear alkane.

The process of this invention can be used in conjunction with other hydrocarbon conversion or refinery processes. For example, normal butane can be converted to C4 olefins and isobutane. The C4 *pl olefins and isobutene can then be upgraded in a refinery alkylation unit to yield high-octane isoparaffinic gasoline blending stock.*

The catalyst composition utilized in accordance with the present invention comprises a platinum metal component and a zincosilicate component.

The zincosilicate component is disclosed in U.S. Pat. No. 4,670,617 (De Simone et al.), the teachings of which are incorporated herein by reference.

The zincosilicate crystalline molecular sieves of this invention are characterized by the representative X-ray diffraction pattern listed in Table I below and by the composition formula:

$$0.9 \pm 0.2\ M_{2/n}O:ZnO:ySiO_2:zH_2O$$

wherein M is at least one cation, n is the valence of the cation, y is between 4 and about 600 and z is between 0 and about 160. It is believed that the small zinc content of the sieves is at least in part incorporated in the crystalline lattice. Various attempts to remove the zinc from the zincosilicate sieves by exhaustive exchange with sodium, ammonium and hydrogen ions were unsuccessful and therefore, the zinc content is considered nonexchangeable in the instant sieves.

TABLE I

| d-Spacing Angstrom (1) | Assigned Strength (2) | d-Spacing Angstrom (1) | Assigned Strength (2) |
|---|---|---|---|
| 11.34 ± 0.20 | VS | 3.87 ± 0.10 | MS |
| 10.21 ± 0.20 | MS | 3.84 ± 0.10 | W |
| 10.10 ± 0.20 | MS | 3.83 ± 0.10 | M |
| 9.88 ± 0.20 | W | 3.77 ± 0.10 | W |
| 6.05 ± 0.20 | W | 3.73 ± 0.10 | M |
| 5.75 ± 0.20 | W | | |

(1) Copper K alpha radiation 
(2) VW = very weak; W = weak; M = medium; MS = medium strong; VS = very strong The zincosilicate molecular sieve useful in this invention can be prepared by crystallizing an aqueous mixture, at a controlled pH, of an organic base, a zinc ion-affording material, an oxide of silicon, and an organic template compound.

Typically, the mole ratios of the various reactants can be varied to produce the crystalline zincosilicates of this invention. Specifically, the mole ratios of the initial reactant concentrations are indicated below:

| | Broad | Preferred | Most Preferred |
|---|---|---|---|
| SiO$_2$/ZnO | 4–200 | 10–150 | 20–100 |
| Organic base/SiO$_2$ | 0.5–5 | 0.05–1 | 0.1–0.5 |
| H$_2$O/SiO$_2$ | 5–80 | 10–50 | 20–40 |
| Template/SiO$_2$ | 0–1 | 0.01–0.02 | 0.02–0.1 |

By regulation of the quantity of zinc (represented as ZnO) in the reaction mixture, it is possible to vary the SiO$_2$/ZnO molar ratio in the final product. In general, it is desirable to have the zinc content of the zincosilicate sieve of this invention between about 0.1 and about 5 percent by weight of zinc. More preferably, the amount of zinc should be between about 0.2 and about 4 wt.% zinc and, most preferably, between about 0.3 and about 3 wt.% of zinc. Too much zinc in the reaction mixture appears to reduce the sieve crystallinity which reduces the catalytic usefulness of the sieve.

More specifically, the material useful in the present invention is prepared by mixing an organic base, a zinc ion-affording substance, an oxide of silicon, and an organic template compound in water (preferably distilled or deionized). The order of addition usually is not critical although a typical procedure is to dissolve the organic base and the zinc ion-affording substance in water and then add the template compound. Generally, the silicon oxide compound is added with intensive mixing such as that performed in a Waring Blender and the resulting slurry is transferred to a closed crystallization vessel for a suitable time. After crystallization, the resulting crystalline product can be filtered, washed with water, dried, and calcined.

During preparation, acidic conditions should be avoided. Advantageously, the pH of the reaction mixture falls within the range of about 8.0 to about 12.0; more preferably between about 9.0 and about 11.0 and most preferably between about 9.5 and 10.5.

Examples of oxides of silicon useful in this invention include silicic acid; sodium silicate; tetraalkyl silicates and Ludox, a stabilized polymer of silicic acid manufactured by E. I. DuPont de Nemours & Co. Typically, the oxide of zinc source is a water-soluble zinc compound such as zinc nitrate or zinc acetate or another zinc compound, the anion of which is easily removed during sieve calcination prior to use.

Cations useful in formation of the zincosilicate sieves include the zinc ion and the hydrogen ion. The sieves are prepared directly in the hydrogen form with an organic base such as ethylenediamine. In the case of the instant zincosilicates, some of the zinc may be present in part as a substitute counter ion for the hydrogen ion. The acidity of these sieves is low as measured by the Hammett H$_o$ function which lies in the neighborhood of about +3 to about +6.

Organic templates useful in preparing the crystalline zincosilicate include alkylammonium cations or precursors thereof such as tetraalkylammonium compounds, especially tetra-n-propylammonium compounds. A useful organic template is tetra-n-propylammonium bromide. Diamines, such as hexamethylenediamine, can be used.

The crystalline zincosilicate molecular sieve can be prepared by crystallizing a mixture of sources for an oxide of silicon, an oxide of zinc, an alkylammonium compound and ethylenediamine such that the initial reactant molar ratios of water to silica range from about 5 to about 80, preferably from about 10 to about 50 and most preferably from about 20 to about 40. In addition, preferable molar ratios for initial reactant silica to oxide of zinc range from about 4 to about 200, more preferably from about 10 to about 150 and most preferably from about 20 to about 100. The molar ratio of ethylenediamine to silicon oxide should be above about 0.05, typically below about 5, preferably between about 0.05 and about 1.0 and most preferably between about 0.1 and about 0.5. The molar ratio of alkylammonium compound, such as tetra-n-propylammonium bromide, to silicon oxide can range from 0 to about 1 or above, typically above about 0.005, preferably about 0.01 to about 0.2, most preferably about 0.02 to about 0.1.

The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about one to about seven days, at a temperature ranging from about 100° to about 250° C., preferably about 125° to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about three to about seven days. Samples of material can be removed during crystallization to check the degree of crystallization and determine the optimum crystallization time.

The crystalline material formed can be separated and recovered by well-known means such as filtration with aqueous washing. This material can be mildly dried for anywhere from a few hours to a few days at varying temperatures, typically about 50° to about 225° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, the mildly dried product is calcined at temperatures ranging from about 260° to about 850° C. and preferably from about 425° to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 to 16 hours. The zincosilicate sieves thus made, generally have a surface area greater than about 300 sq. meters per gram as measured by the BET procedure.

The zincosilicate sieve useful in this invention is admixed with or incorporated within various binders or matrix materials depending upon the intended process use. The crystalline zincosilicates are combined with active or inactive materials, synthetic or naturally-occurring zeolites, as well as inorganic or organic materials which would be useful for binding the zincosilicate. Well-known materials include silica, silica-alumina, alumina, magnesia, titania, zirconia, alumina sols, hydrated aluminas, clays such as bentonite or kaolin, or other binders well-known in the art. Typically, the zincosilicate is incorporated within a matrix material by blending with a sol of the matrix material and gelling the resulting mixture or slurrying the sieve with the matrix material and drying. Also, solid particles of the zincosilicate and matrix material can be physically admixed. Typically, such zincosilicate compositions can be pelletized or extruded into useful shapes. The crystalline zincosilicate content can vary anywhere from a few up to 100 wt.% of the total weight of zincosilicate plus matrix. More specifically, the zincosilicate is present from about 0.1 wt.% to about 100 wt.%, preferably from about 10 wt.% to about 95 wt.% and most preferably from about 20 wt.% to about 80 wt.% of such zincosilicate based on the total weight of zincosilicate and matrix.

More specifically, catalytic compositions comprising the crystalline zincosilicate material of this invention and a suitable matrix material are formed by adding a finely-divided crystalline zincosilicate sieve to an aqueous sol or gel of the matrix material, such as PHF Alumina made by American Cyanamid Co. The resulting mixture is thoroughly blended and gelled, typically by adding a material such as ammonium hydroxide. The resulting gel is dried below about 200° C., more preferably between about 100° C. and about 150° C. and calcined between about 350° C. and about 700° C. to form a catalyst composition in which the crystalline zincosilicate sieve is distributed throughout the matrix material.

Alternatively, the sieve and a suitable matrix material like alpha-alumina monohydrate such as Conoco Catapal SB Alumina can be slurried with a small amount of a dilute weak acid such as acetic acid, dried at a suitable temperature under about 200° C., preferably about 100° C. to about 150° C., and then calcined at between about 350° C. and about 700° C., more preferably between about 400° C. to about 650° C. The platinum metal component can be added to the zincosilicate by ion exchange, impregnation, or combination thereof, or other suitable contact means.

Ion-exchange and impregnation techniques are well-known in the art. Typically, an aqueous solution of a cationic species is exchanged one or more times at about 25° to about 100° C. A hydrocarbon-soluble metal compound such as a metal carbonyl also can be used to place a catalytically active material. Impregnation of the platinum metal component on the zincosilicate or the zincosilicate distributed in and throughout the matrix support component results in a suitable catalyst composition.

The amount of platinum metal group component contained in the final composite can vary from about 0.01 to about 10 wt.%, typically from about 0.05 to about 5 wt.%, and most preferably from about 0.05 to about 1.0 wt.% calculated as the zero valent metal and based on the total weight of the entire catalyst composition.

In a process using this invention, a stream of an alkane, such as n-butane, is contacted with the catalyst of the present invention. Generally, in the preferable process of this invention a linear alkane or molecule containing a linear alkane segment is contacted with the above-described catalyst system in the vapor phase at a suitable reaction temperature, pressure and space velocity. Generally, suitable reaction conditions include a temperature of about 250° to about 650° C, a pressure of about 0.1 to about 50 atmospheres (10 to 5,000 kPa) or higher with hydrogen/hydrocarbon molar ratio of 0 to about 10 or higher at a weight hourly space velocity (WHSV) of about 0.1 to about 40 $hr^{-1}$.

As has been previously mentioned, the process of the present invention can be carried out in the absence of hydrogen or at a relatively low hydrogen partial pressure without adversely affecting the stability, i.e., activity maintenance of the catalyst. In a typical process scheme, an n-butane-containing hydrocarbon stream is contacted with such catalyst in a reactor at about 400° to about 600° C. at a pressure of about 0.2 to about 20 atmospheres (20 to 2000 kPa) with a hydrogen/butane molar ratio of 0 to about 10 at a WHSV of about 0.3 to about 25 $hr^{-1}$. Preferably, the n-butane conversion process of this invention is conducted at about 450° to about 600° C. at a pressure of about 0.3 to about 5 atmospheres (30 to 200 kPa) with a hydrogen/butane molar ratio of about 0 to about 6 at a WHSV of about 1 to about 15 hr$^{-1}$.

Although conversion of n-butane is the preferable process of this invention, propane and ethane similarly can be converted to propylene and ethylene although more severe conditions (higher temperature and lower pressures and lower space velocities) typically are used. For conversion of ethane and propane, preferable conditions are temperatures at about 500° to about 650° C., space velocities of about 0.5 to about 10 hr$^{-1}$ and pressures of about 0.1 to about 2 atmospheres.

The present invention is described in further detail in connection with the following Example, it being understood that the example is for purposes of illustration and not limitation.

EXAMPLE

The platinum/zincosilicate catalyst used for n-butane conversion in accordance with the present invention was prepared as elucidated below. The zincosilicate molecular sieve was synthesized according to the teachings in U.S. Pat. No. 4,670,617 (De Simone et al.). The ammonium form of the zincosilicate molecular sieve was calcined at 1000° F. to convert it to the protonic form. An analysis of the zincosilicate is set out in Table II below.

TABLE II

| ANALYSES OF ZINCOSILICATE MOLECULAR SIEVE | |
|---|---|
| Composition | Wt. % |
| Zn | 1.06 |
| Na | 0.124 |
| Al | 0.140 |
| Si | 31.5 |

The zincosilicate was subsequently dry-mixed with Catapal alumina (alpha-alumina monohydrate) at a weight ratio of 60% molecular sieve at 40% alumina. Dilute acetic acid (5% concentration) was blended slowly into the powder mixture of zincosilicate and alumina until a paste formed. During the addition of acetic acid, the zincosilicate and alumina mixture were continually stirred. The paste was then dried in a vacuum oven at 70° C. overnight, followed by calcination under air flow in a muffle furnace at 1100° F. for 18 hours. The zincosilicate-alumina solid was then comminuted and sieved to obtain 10-20 mesh range particles.

Platinum was added to the zincosilicate-alumina particles by the method of incipient wetness impregnation of the solid particles from an aqueous solution of tetraamine platinum (II) nitrate. A sufficient concentration of tetraamine platinum (II) nitrate in the impregnation solution was used, so that the loading of elemental platinum in the composite was 0.1 wt.%. After impregnation, the particles were dried in a vacuum oven at 70° C. overnight followed by calcination under air flow at 1000° F. for two hours. The platinum/zincosilicate catalyst was then stored in a jar until use.

The platinum/zincosilicate catalyst was evaluated for n-butane conversion in accordance with the process of the invention in a continuous-flow, down-flow, single-pass, fixed-bed reactor at the following conditions:

Temperature = 1000° F.
Pressure = 50 psig
Feed = 100% n-Butane
WHSV = 9 hr$^{-1}$ Prior to reaction, the catalyst was pretreated by first drying in nitrogen flow for 0.5 hour at 1000° F., followed by reduction in hydrogen flow for one hour at 1000° F., followed by a nitrogen purge for 0.25 hour at 1000° F.

The results and conditions for the conversion of n-butane on platinum/zincosilicate catalyst in accordance with the present invention are presented in Table III below.

TABLE III n-Butane Conversion on Pt/Zn-Silicate

| Catalyst | | | | | | | | | | | | | | | |
|---|---|---|---|---|---|---|---|---|---|---|---|---|---|---|---|
| Temperature, °F. | | | | | | Pt/Zn-silicate | | | | | | | | | |
| Reactor pressure, psig | | | | | | 1000 | | | | | | | | | |
| Feed | | | | | | 50 | | | | | | | | | |
| WHSV | | | | | | 100% n-Butane | | | | | | | | | |
| | | | | | | 9 | | | | | | | | | |

| Time-on-stream, h | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Conversion, wt. % | 41.6 | 37.2 | 35.0 | 34.1 | 34.0 | 32.7 | 32.0 | 31.7 | 30.7 | 30.8 | 30.5 | 30.2 | 30.0 | 30.1 | 29.8 |
| Hydrocarbon distribution, wt. % | | | | | | | | | | | | | | | |
| $C_1$ | 0.7 | 0.7 | 0.7 | 0.7 | 0.7 | 0.7 | 0.7 | 0.7 | 0.7 | 0.6 | 0.6 | 0.6 | 0.7 | 0.6 | 0.6 |
| $C_2$ | 2.5 | 2.3 | 2.2 | 2.2 | 2.2 | 2.0 | 2.0 | 2.0 | 2.1 | 1.9 | 2.0 | 2.0 | 2.1 | 1.9 | 1.9 |
| $C_3$ | 14.0 | 10.6 | 9.0 | 8.5 | 8.6 | 7.2 | 6.8 | 6.5 | 7.0 | 5.7 | 5.6 | 5.6 | 6.3 | 5.3 | 5.2 |
| Isobutane | 15.5 | 11.6 | 9.5 | 8.9 | 9.2 | 7.2 | 6.4 | 6.0 | 7.1 | 5.2 | 5.0 | 4.8 | 6.1 | 4.6 | 4.3 |
| Isobutene + Butene-1 | 18.6 | 22.9 | 24.7 | 25.4 | 24.8 | 26.6 | 27.2 | 27.6 | 26.4 | 28.4 | 28.7 | 28.8 | 27.5 | 28.9 | 29.2 |
| trans-Butene-2 | 12.6 | 17.0 | 19.3 | 20.3 | 20.2 | 22.4 | 23.4 | 24.0 | 23.0 | 25.3 | 25.8 | 26.0 | 24.7 | 26.5 | 26.9 |
| cis-Butene-2 | 9.5 | 12.8 | 14.6 | 15.3 | 15.2 | 16.8 | 17.5 | 18.0 | 17.3 | 19.1 | 19.4 | 19.6 | 18.6 | 19.9 | 20.3 |
| $C_5$-$C_6$ aliphatics | 12.9 | 10.6 | 10.1 | 9.5 | 9.5 | 8.6 | 8.0 | 8.1 | 8.9 | 7.8 | 7.3 | 7.2 | 7.9 | 6.5 | 6.7 |
| Benzene | 0.9 | 0.7 | 0.5 | 0.5 | 0.6 | 0.5 | 0.4 | 0.3 | 0.3 | 0.2 | 0.2 | 0.2 | 0.4 | 0.3 | 0.2 |
| Toluene | 2.2 | 1.6 | 1.3 | 1.2 | 1.2 | 1.0 | 1.1 | 0.8 | 0.9 | 0.7 | 0.7 | 0.6 | 0.7 | 0.7 | 0.6 |
| Xylenes | 9.1 | 8.0 | 7.1 | 6.7 | 7.0 | 6.3 | 6.3 | 5.4 | 5.6 | 4.7 | 4.4 | 4.2 | 4.5 | 4.5 | 3.8 |
| $C_9$ + aromatics | 1.5 | 1.2 | 1.0 | 0.8 | 0.8 | 0.7 | 0.6 | 0.6 | 0.7 | 0.4 | 0.3 | 0.4 | 0.5 | 0.3 | 0.3 |

The above Table III shows that as the catalyst attained steady-state performance after about 12 hours on stream, it manifested a fractional conversion of about 30 wt.% with the following hydrocarbon product selectivities: 2.5 wt.% $C_1$ and $C_2$, 5 wt.% $C_3$, 4.5 wt.% isobutane, 29 wt.% isobutene and butene-1, 47 wt.% cis- and trans-butene-2, 7 wt.% $C_5$-$C_6$ aliphatics, and 5 wt.% gasoline range aromatics.

It should be noted that dehydrogenation equilibrium constraint at the above reaction conditions, i.e., temperature and pressure, dictates the presence of dehydrogenation products at approximately the levels reported above for the process of the invention using the platinum/zincosilicate catalyst at steady-state catalytic performance.

As mentioned above, yields of dehydrogenation products can be increased by increasing the temperature and decreasing the pressure High temperatures and low pressures affect dehydrogenation equilibria favorably. All products other than $C_1$–$C_3$ products are of higher value than the n-butane feedstock. The $C_1$–$C_3$ products can be relatively easily separated from the $C_4+$ products, while the $C_5+$ gasoline blending stock can also be relatively easily separated from the $C_4$ with methods known to those skilled in the art.

The $C_4$ product stream, which is predominantly olefinic, can be used for alkylation which reacts butenes with isobutane to yield high-octane isoparaffinic gasoline blending stock. Alternatively, the $C_4$ product stream can be passed to a methyl tertiary butyl ether (MTBE) unit where isobutene is selectively reacted; the remaining butenes and isobutane can then be passed to an alkylation unit.

A comparative experiment was carried out to convert n-butane with a conventional platinum/alumina catalyst system obtained from a catalyst vendor under the same conditions and catalyst pretreatment steps set out above.

The platinum/alumina catalyst used for the comparative experiment contained nominally 0.8 wt.% Pt and 0.9 wt.% Cl supported on gamma-alumina. This catalyst in extrudate form was comminuted and sieved to obtain 10–20 mesh range particles for testing. Catalytic results for n-butane conversion in the presence of a platinum/alumina catalyst are presented in Table IV below.

TABLE IV

| n-Butane Conversion with Pt/Al$_2$O$_3$ (Comparative) | | | | |
|---|---|---|---|---|
| Catalyst | Pt/Al$_2$O$_3$ | | | |
| Temperature, °F. | 1000 | | | |
| Reactor pressure, psig | 50 | | | |
| Feed | 100% n-Butane | | | |
| WHSV | 9 | | | |
| Time-on-stream, h | 1 | 2 | 3 | 4 |
| Conversion, wt. % | 27.1 | 18.4 | 14.4 | 12.1 |
| Hydrocarbon distribution, wt. % | | | | |
| $C_1$ | 4.4 | 3.9 | 4.0 | 4.3 |
| $C_2$ | 5.3 | 5.1 | 5.4 | 6.0 |
| $C_3$ | 6.7 | 5.5 | 5.5 | 6.0 |
| Isobutane | 6.3 | 3.5 | 2.7 | 2.2 |
| Isobutene + Butene-1 | 36.1 | 39.6 | 40.2 | 39.9 |
| trans-Butene-2 | 17.8 | 20.2 | 20.8 | 20.8 |
| cis-Butene-2 | 13.3 | 15.0 | 15.4 | 15.4 |
| $C_5$—$C_6$ aliphatics | 3.8 | 2.8 | 2.0 | 2.1 |
| Benzene | 0.6 | 0.5 | 0.4 | 0.3 |
| Toluene | 1.7 | 1.2 | 1.1 | 1.0 |
| Xylenes | 3.2 | 2.4 | 2.2 | 1.9 |
| $C_9$ + aromatics | 0.8 | 0.3 | 0.3 | 0.1 |

It is evident from a comparison of Tables III and IV, that platinum/alumina shows a higher rate of deactivation than platinum/zincosilicate system employed in the process of the invention. The superior stability of the platinum/zincosilicate system over the conventional platinum/alumina is further illustrated in FIG. 1, which plots fractional n-butane conversion versus time-on-stream using data presented in Tables III and IV.

The platinum/alumina based system also shows poorer product selectivity than platinum/zincosilicate. The selectivity to low-valued $C_1$–$C_3$ by-products for platinum/alumina based system is doubled that for invention platinum/zincosilicate system. The selectivity to high-valued aromatics is lower for platinum/alumina. While the selectivity towards total $C_4$ monoolefins is comparable for the comparative versus invention processes, the platinum/zincosilicate system is more active It should also be emphasized that the platinum/zincosilicate catalyst system contained only one-eighth the loading of platinum in the platinum/alumina catalyst.

In summary, the process of the invention using a platinum/zincosilicate catalyst for n-butane conversion is highly selective for dehydrogenation to yield $C_4$ monoolefins. Other high-valued products including isobutane and $C_5+$ gasoline range hydrocarbons concentrated in BTX aromatics are simultaneously produced in lower concentrations. The platinum/zincosilicate catalyst is more stable and active than a conventional platinum/alumina catalyst which contains considerably more platinum. In addition, platinum/zincosilicate catalyst is more selective in producing $C_4$ and heavier products than platinum/alumina from the n-butane feedstock.

What is claimed is:

1. A process to convert a substantially linear alkane to dehydrogenated and isomerized products comprising contacting such alkane under conversion conditions with a catalyst composition comprising a platinum metal component and a zincosilicate component comprising a high surface area, crystalline silica molecular sieve, essentially aluminum free and containing between about 0.1 wt.% and about 5 wt.% nonexchangeable zinc, composited in an inorganic matrix, said sieve made by crystallization from an aqueous solution containing an organic base, an organic templating material, a zinc ion-affording material and an oxide of silicon and providing an X-ray pattern comprising the following X-ray diffraction lines and assigned strengths:

| Interplanar Spacing d, Angstrom | Assigned Strength | Interplanar spacing d, Angstrom | Assigned Strength |
|---|---|---|---|
| 11.34 ± 0.20 | VS | 3.87 ± 0.10 | MS |
| 10.21 ± 0.20 | MS | 3.84 ± 0.10 | W |
| 10.10 ± 0.20 | MS | 3.83 ± 0.10 | M |
| 9.88 ± 0.20 | W | 3.77 ± 0.10 | W |
| 6.05 ± 0.20 | W | 3.73 ± 0.10 | M |
| 5.75 ± 0.20 | W | | |

2. The process of claim 1 wherein the substantially linear alkane comprises a normal alkane having two to twenty carbon atoms or an organic compound containing a linear alkane segment having three to twenty carbon atoms.

3. The process of claim 2 wherein the alkane is a normal alkane having two to twenty carbon atoms or an isoalkane containing a linear alkane segment having three to twenty carbon atoms.

4. The process of claim 1 wherein the alkane is a normal alkane having two to about twenty carbon atoms.

5. The process of claim 4 wherein the linear alkane is ethane, n-propane, n-butane, n-pentane or n-hexane.

6. The process of claim 5 wherein the linear alkane is n-butane.

7. The process of claim 5 wherein the substantially linear alkane comprises from about 10 to 100 wt.% of a feedstream contacting the catalyst.

8. The process of claim 1 wherein the platinum metal component is present in an amount ranging from about 0.01 to about 10 wt.% calculated as the zero valent metal and based on the total weight of the composition.

9. The process of claim 8 wherein the platinum metal component is present in an amount ranging from about 0.05 to about 5 wt.% calculated as the zero valent metal and based on the total weight of the composition.

10. The process of claim 9 wherein the platinum metal component is present in an amount ranging from about 0.05 to about 1.0 wt.% calculated as the zero valent metal and based on the total weight of the composition.

11. The process of claim 7 wherein the platinum group metal is present in an amount ranging from about 0.05 to about 1.0 wt.% calculated as the zero valent metal and based on the total weight of the composition.

12. The process of claim 1 wherein the inorganic matrix is silica, silica-alumina, or alumina.

13. The process of claim 12 wherein the inorganic matrix is alumina.

14. The process of claim 7 wherein the inorganic matrix is alumina.

15. The process of claim 7 wherein the zincosilicate component is present in an amount ranging from about 10 to about 95 wt.% based on the total weight of the zincosilicate component and the inorganic matrix.

16. The process of claim 1 wherein the zincosilicate component is present in an amount ranging from about 10 to about 95 wt.% based on the total weight of the zincosilicate component and the inorganic matrix.

17. A process to convert n-butane to a mixture comprising dehydrogenated and isomerized products comprising contacting n-butane under conversion conditions with a catalyst composition comprising a platinum metal component present in an amount ranging from about 0.05 to about 1.0 wt.% based on the total weight of the catalyst composition and a zincosilicate component comprising a high surface area, crystalline silica molecular sieve, essentially aluminum free and containing between about 0.2 wt.% and about 4 wt.% nonexchangeable zinc, composited in an inorganic matrix, said sieve made by crystallization from a solution containing ethylenediamine, tetrapropylammonium bromide, zinc acetate or nitrate, and an oxide of silicon, and providing an X-ray pattern comprising the following X-ray diffraction lines and assigned strengths:

| Interplanar Spacing d, Angstrom | Assigned Strength | Interplanar Spacing d, Angstrom | Assigned Strength |
|---|---|---|---|
| 11.34 ± 0.20 | VS | 3.87 ± 0.10 | MS |
| 10.21 ± 0.20 | MS | 3.84 ± 0.10 | W |
| 10.10 ± 0.20 | MS | 3.83 ± 0.10 | M |
| 9.88 ± 0.20 | W | 3.77 ± 0.10 | W |
| 6.05 ± 0.20 | W | 3.73 ± 0.10 | M |
| 5.75 ± 0.20 | W | | |

18. The process of claim 17 wherein the zincosilicate component is present in an amount ranging from about 10 to about 95 wt.% based on the total weight of the zincosilicate component and the inorganic matrix.

19. The process of claim 18 wherein the inorganic matrix is alumina.

* * * * *